United States Patent [19]

Abbruzzese et al.

[11] 4,058,613
[45] Nov. 15, 1977

[54] QUINOLINE DERIVATIVES HAVING FUNGICIDAL ACTIVITY

[75] Inventors: Luigi Abbruzzese, Milan; Franco Gozzo, Saronno (Varese); Giorgio Rossi; Marcella Masoero, both of Milan; Simone Lorusso, San Giuliano Milanese (Milan); Paola Bonola, Milan; Gino Tamburin, San Donato Milanese (Milan), all of Italy

[73] Assignee: Montedison S.p.A., Milan, Italy

[21] Appl. No.: 677,248

[22] Filed: Apr. 15, 1976

[30] Foreign Application Priority Data

Apr. 15, 1975 Italy .................................. 22348/75

[51] Int. Cl.$^2$ .............................................. A01N 9/22

[52] U.S. Cl. .................................................... 424/258
[58] Field of Search ......................................... 424/258

[56] References Cited

U.S. PATENT DOCUMENTS 2,802,771   8/1957   Fields et al. ........................ 424/258

FOREIGN PATENT DOCUMENTS 490,021   6/1970   Switzerland

*Primary Examiner*—V. D. Turner

[57] ABSTRACT

Quinoline derivatives having fungicidal action and, more particularly, quinoline derivatives quaternarized to the nitrogen atom and effective against peronospora, oidium, and Botrytis, are disclosed.

6 Claims, No Drawings

QUINOLINE DERIVATIVES HAVING FUNGICIDAL ACTIVITY

THE PRIOR ART

It is known (Albert; Selective Toxicity, 5th Ed. 1973, p. 370, 10.7) that while 8-hydroxy quinoline has antibacterial activity in vitro, neither the O-alkyl nor the N-alkyl derivatives exhibit any activity (Albert, supra, pp. 370–377).

Nitrogen protonated salts of 8-hydroxyquinoline active against fungi are disclosed in Swiss Patent No. 490,021. However, those salts are quinoline derivatives in which both the nitrogen atom and the hydroxyl group are free or at any rate in equilibrium, in an aqueous solution, with a free basic form.

As shown by experimental data in said Swiss patent, 8-hydroxy-quinoline exhibits no activity in vivo with respect to Botrytis infesting vines, either as such or in the form of non-quaternarized salts.

THE PRESENT INVENTION

An object of this invention is to provide derivatives of quinoline and of 8-hydroxy-quinoline which are effective in preventing or combatting infections by, specifically, *Botrytis cinerea pers., Plasmopara viticola* (B. et C.) *Berl et de Toni*, and *Sphaerotheca fuliginea* (Schlech) Salmon.

The active fungicides of the invention, which are derivatives of quinoline and of 8-hydroxy-quinoline having substituents on the N atom, have the general formula

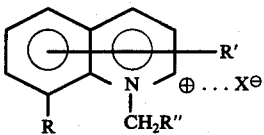

(I)

in which

R is H or OH;

R' is H, a lower alkyl radical, or a halogen atom;

R" is H, $C_2H_5$, or $4ClC_6H_4-$, and X is an anion.

It is known that when, in the foregoing formula (I), R is OH, the elimination of HX acids results in the formation of betainic compounds of the general formula

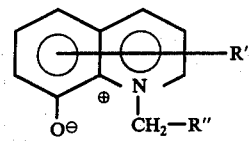

(II)

We have found that the betainic compounds of formula (II) are also active fungicides, similarly to the compounds of formula (I).

The quinoline derivatives of the formulae given are known chemical substances. The substitution on the N atom is obtained by reacting the quinoline derivative with the halide of the selected substituent in a suitable solvent and according to the reaction:

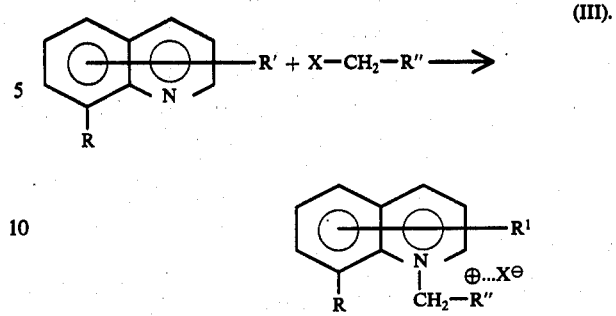

(III).

in which R, R' and R" have the same meaning as in formula (I), and X is halogen.

The compounds of formula (III) are crystalline and, in general, soluble in water and insoluble in non-polar solvents. They can be purified by recrystallization from polar solvents, for instance alcohol, or from other suitable solvents.

Specific compounds which have been found to exhibit the fungicidal activity according to the invention, include the following compounds having the melting points given and purified by recrystallization from the solvents indicated:

| Compound | M.P.° C - | Recrystallization Solvent |
|---|---|---|
| 8-hydroxy-quinolinum-N-methyliodide | 172–173 | ethanol |
| 4-methyl-quinolinum-N-methyliodide | 177–178 | ethanol |
| quinolinum-N-methyl-iodide | 136–137 | ethanol |
| quinolinum-N-(p-chlorobenzyl) chloride | 139–141 | ethanol + acetone (2/6 Vol/Vol.) |

The identity of the compounds was determined by examination of the I.R. spectra.

All of the compounds of formula (III) which were tested were found to have anti-fungal activity in vivo against *Botrytis cinerea, Plasmopara viticola* and *Sphaerotheca fuliginea*. However, the activity varied depending on the specific fungus, some compounds being more active against one species of fungus, other compounds being more active against another species.

The compounds found to function as fungicides according to the invention act through the foliage and are anti-fungal in that they both effectively combat the fungi mentioned after infestation of the plants and also function to prevent such infestation by direct contact, as is evident from Example 5 below.

The following examples are given to illustrate the invention and are not intended as limiting.

EXAMPLE I 8-hydroxy-quinolinium-N-methyl-iodide was prepared by treating 4.3 g (0.03 moles) of 8-hydroxyquinoline with 22.8 g (0.16 moles) of methyl iodide and 10 cc of ethanol.

This solution was reflux-heated under constant stirring for 4 hours, after which 150 cc of ethyl ether were added.

A solid precipitated from the solution. It was filtered, washed with ether and then crystallized from ethanol, thereby yielding 3.5 of yellow, hydrosoluble crystals having a melting point of 172°–173° C.

Elementary analysis: Theoretical I−= 44.20%; found I−= 44.87%. The IR spectrum showed bands characteristics for 8-hydroxyquinolinium-N-methyliodide.

EXAMPLES II–IV

Using the same method as in Example I, the following compounds were prepared and characterized by examination of the IR spectrum:

4-methylquinolinium-N-methyliodide, m.p. 177°–178° C. theoretical I−= 44.51%; found I³¹ = 43.70%.

quinolinium-N-methyliodide, m.p. 136°–137° C. theoretical I−= 46.81%; found I−= 47.53%.

quinolinium-N-(p-chlorobenzyl)chloride, m.p. 139°–141° C (from ethanol and acetone 2:6, vol/vol). theoretical Cl−= 12.22%; found Cl−= 11.47%. theoretical N = 4.82%; found N = 4.59%.

The IR and NMR spectra of the above listed compounds are in accordance with the above cited formulae.

EXAMPLE V

Determination of the activity:
Protective activity in tomato plants on *Botrytis cinerea pers.*

Both leaf faces of tomato plants cv. Marmande, grown in pots in a conditioned environment, were uniformly sprayed with an aqueous or hydroacetonic solution at 20% acetone (vol/vol) containing 1.5% of the products under examination, up to the limit of dripping from the leaves. After one day, artificial infection was carried out by inoculating both foliar faces with a suspension in a carrot broth of *Botrytis cinerea* (1,000,000 spores per cc). At the end of the incubation period (7 days) the gravity of the infection was evaluated by sight with ratings from an evaluation scale ranging from 100 (for a healthy plant) to 0 (for a completely infected plant).

Curative activity through foliage on *Plasmopara viticola* (B. et C) *Berl et de Toni.*

The leaves of vine cv. Dolcetto, grown in pots in a conditioned environment, were sprinkled uniformly on the lower faces of the leaves with an aqueous solution of conidia of *Plasmopara viticola* (200,000 conidia per cc.).

After 24 hours permanence in a moisture saturated environment, said leaves were treated with the aqueous or hydroacetonic 1.5% solution of the products under examination, by sprinkling both foliar faces.

After a 7 day incubation, the percentage of foliar surface not invaded by the fungus was evaluated according to the previously cited scale.

Curative Activity Through Foliage in Cucumber Plants on *Sphaerotheca Fuliginea* (Schlech) Salmon The upper faces of leaves of cucumber plants cv. Marketer, grown in pots in a conditioned environment, were uniformly sprinkled with an aqueous solution of *Sphaerotheca fuliginea conidia* (200,000 conidia per cc.). After 24 hours, said leaves were treated as previously described by sprinkling an aqueous or hydroacetonic solution of the product under examination in a 1.5% concentration, on both foliar faces.

After an 8 day incubation, the gravity of the infection was evaluated by sight with the help of a value scale ranging from 100 (corresponding to a healthy plant) to 0 (equal to a completely infected plant).

The results thus obtained are recorded in the Table.

TABLE

Coefficients of fungicide activity on plants of compounds of the general formula:

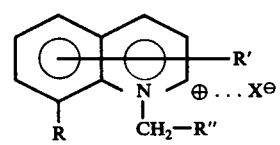

| R | R' | R'' | X |
|---|----|-----|---|
| H | H | H | I |
| H | H | H | I |
| H | 4-me | H | I |
| O | H | H*** | |
| H | H | 4-Cl-Ph | Cl |

| Activity % for a dose of 1.5% (untreated control = 0) | | |
|---|---|---|
| Plant: Tomato | Vine | Cucumber |
| Fungus: *Botrytis c.* | *Plasmopara v.* | *Sphaerotheca f.* |
| Type of Action: Preventive | Curative | Curative |
| 50* | 0 | 0 |
| 32 | 0 | 100 |
| 54 | 0 | 0 |
| 60 | 60 | 100** |

*The quantities of active substance per sq.cm. of foliar surface treated amounted to 15 micrograms.

**The quantities of active substance per sq.cm. of treated foliar surface amounted to 30 micrograms.

***Betaine derived from 8-hydroxyquinolinium-N-methyl-iodide by elimination of HI.

The anti-fungal agents of the invention can be applied to the plants to be treated in the form of solutions, suspensions or dispersions, or as powders which may comprise various carriers or fillers of the kind conventionally used in preparing such powders.

We claim:

1. A method for combatting or preventing infections of plants by *Botrytis cinerea pers., Plasmopara Viticola* (B. et C), *Berl et de Toni,* and *Sphaerotheca fulginea* (Schlech) Salmon, which comprises sprinkling on the leaves of the plant to be protected an aqueous solution or suspension of an active anti-fungal agent which is a quinolinic derivative of the general formula (I)

wherein:
R = OH or H;
R' = H or C₁-C₅alkyl;
R'' = H; C₂H₅; or 4 Cl—C₆H₄; and
X = halogen
in such quantities that the amount of the quinolinic derivative deposited on the leaves is equal to or greater than 15 mg/sq cm of leaf.

2. The method of claim 1, in which the active anti-fungal agent is a betaine derivative resulting from the elimination of the HX acid from a quinoline derivative of formula (I) in which R is OH, according to the reaction

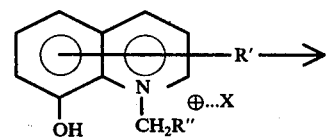

-continued

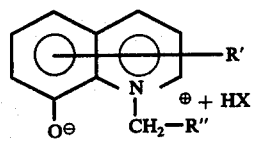

3. The method of claim 1, in which the active antifungal agent is 8-hydroxy-quinolinium-N-methyliodide or the corresponding betaine.

4. The method of claim 1, in which the active antifungal agent is 4-methyl-quinolinium-N-methyliodide.

5. The method of claim 1, in which the active antifungal agent is quinolinium-N-methyliodide.

6. The method of claim 1, in which the active antifungal agent is quinolinium-N-(p.chlorobenzyl)chloride.

* * * * *

UNITED STATES PATENT OFFICE
CERTIFICATE OF CORRECTION

Patent No. 4,058,613      Dated November 15, 1977

Inventor(s) Luigi ABBRUZZESE et al

It is certified that error appears in the above-identified patent and that said Letters Patent are hereby corrected as shown below:

Col. 2, line 67,    "3.5 of yellow, hydrosoluble crystals ---" should read

- - - 3.5 g of yellow, hydrosoluble crystals - - -,

Col. 3, Examples II-IV, lines 10-11,

"found $I^{31}$ = 43.70%." should read

- - - found $I^-$ = 43.70% - - -.

Signed and Sealed this

Fifteenth Day of May 1979

[SEAL]

Attest:

RUTH C. MASON
Attesting Officer

DONALD W. BANNER
Commissioner of Patents and Trademarks